United States Patent [19]
Kuroda et al.

[11] Patent Number: 6,043,383
[45] Date of Patent: Mar. 28, 2000

[54] PROCESS FOR PRODUCING 1,2-EPOXY-5,9-CYCLODODECADIENE

[75] Inventors: Nobuyuki Kuroda; Mitsuo Yamanaka; Osamu Yamazaki; Hirofumi Takemoto; Kohei Ninomiya; Junichi Kugimoto; Koji Kaiso; Hideo Shimomura, all of Ube, Japan

[73] Assignee: Ube Industries, Ltd., Ube, Japan

[21] Appl. No.: 09/290,500

[22] Filed: Apr. 12, 1999

[30] Foreign Application Priority Data

Apr. 15, 1998 [JP] Japan .................................. 10-102709

[51] Int. Cl.[7] ...................... C07D 303/06; C07D 301/16; C07D 301/12
[52] U.S. Cl. ............................ 549/513; 549/526; 549/531
[58] Field of Search ..................... 549/513, 526, 549/531

[56] References Cited

U.S. PATENT DOCUMENTS

| | | | |
|---|---|---|---|
| 4,423,239 | 12/1983 | Miyazaki et al. | 549/541 |
| 4,562,276 | 12/1985 | Venturello et al. | |
| 4,595,671 | 6/1986 | Venturello et al. | |
| 5,086,189 | 2/1992 | Lecloux et al. | 549/531 |
| 5,274,140 | 12/1993 | Venturello et al. | |
| 5,286,885 | 2/1994 | Goetz et al. | 549/531 |
| 5,849,937 | 12/1998 | Jubin, Jr. et al. | 549/529 |

FOREIGN PATENT DOCUMENTS

| | | |
|---|---|---|
| 3002838 | 5/1981 | Germany . |
| 4513331 | 5/1970 | Japan . |
| 56-104877 | 8/1981 | Japan . |
| 133471 | 7/1989 | Japan . |
| 374235 | 11/1991 | Japan . |
| 5213919 | 2/1992 | Japan . |

OTHER PUBLICATIONS

Bulletin of the Chemical Society of Japan vol. 42 1604–1608 (1969).
English Abstract corresponding to Japan No. 5,213,919.
English Abstract corresponding to Japan No. 45–13,331.
English Abstract corresponding to Japan No. 56–104,877.

*Primary Examiner*—Alan L. Rotman
*Assistant Examiner*—Rita Desai
*Attorney, Agent, or Firm*—Burgess, Ryan & Wayne

[57] ABSTRACT

1,2-epoxy-5,9-cyclododecadiene is produced with a high selectivity thereto by epoxidizing 1,5,9-cyclododecatriene in a continuous multi-stage oxidation apparatus having a plurality of reactors connected to each other in series in such a manner that (1) in a first reactor, 1,5,9-cyclododecatriene, hydrogen peroxide, catalyst components and optionally a mineral acid are subjected to an epoxidation reaction; (2) the resultant reaction mixture delivered from the first reactor is passed through one or more succeeding reactors to further epoxidize the non-reacted 1,5,9-cyclododecatriene with the non-reacted hydrogen peroxide; and (3) the final reaction mixture produced in a rearend reactor is delivered from the oxidation apparatus, and optionally subjected to an isolation-refining procedure wherein the target 1,2-epoxy-5,9-cyclododecadiene is refined and collected and the non-reacted 1,5,9-cyclododecatriene is recovered and recycled to the epoxidation procedure.

21 Claims, 1 Drawing Sheet

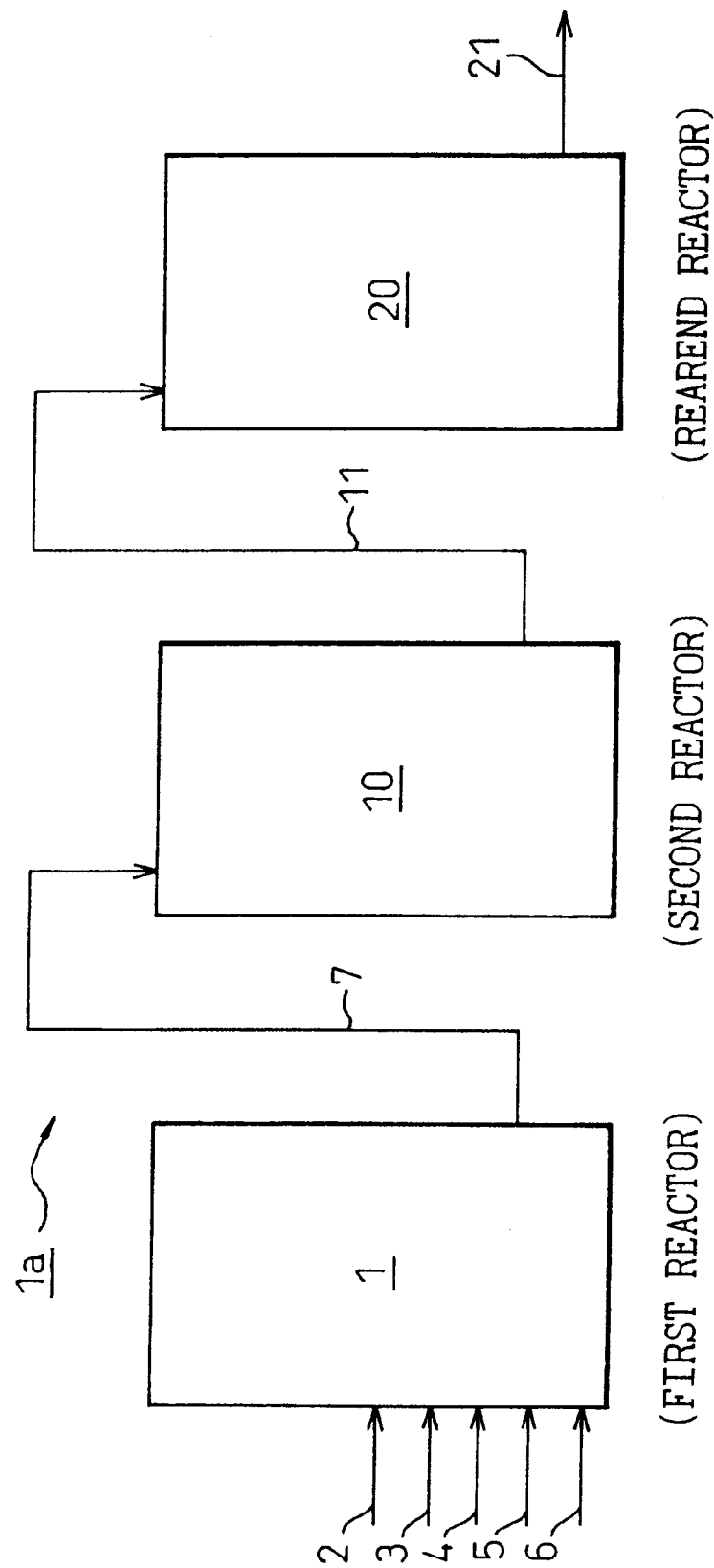

PROCESS FOR PRODUCING 1,2-EPOXY-5,9-CYCLODODECADIENE

BACKGROUND OF THE INVENTION

(1) Field of the Invention

The present invention relates to a process for producing 1,2-epoxy-5,9-cyclododecadiene. Particularly, the present invention relates to a process for producing 1,2-epoxy-5,9-cyclododecadiene by monoepoxidizing 1,5,9-cyclododecatriene with hydrogen peroxide. More particularly, the present invention relates to a process for producing 1,2-epoxy-5,9-cyclododecadiene which has a reactive epoxy group and two carbon-to-carbon double bonds and thus is usable for producing a polymer component of paints or adhesives, and capable of converted to cyclododecanone which can be easily converted, by conventional methods, to lactam compounds, lactone compounds and dibasic carboxylic acids which are important as intermediates of synthetic resins and fibers, for example, polyester and polyamide resins and fibers.

(2) Description of the Related Art

Generally, methods for epoxidizing olefin compounds with hydrogen peroxide are well known. Particularly, the methods for epoxidizing olefin compounds with hydrogen peroxide in the presence of a tungsten compound, a quaternary onium salt and a mineral acid are disclosed in Japanese Examined Patent Publication No. 1-33,471 and No. 3-74,235 and Japanese Unexamined Patent Publication No. 5-213,919. However, none of the above-mentioned Japanese publications teaches a process for producing 1,2-epoxy-5,9-cyclododecadiene by selectively epoxidizing only one carbon-to-carbon double bond of 1,5,9-cyclododecatriene having three carbon-to-carbon double bonds. Also, none of the prior arts disclose an industrial process for producing 1,2-epoxy-5,9-cyclododecadiene from 1,5,9-cyclododecatriene with a high productivity.

Japanese Examined Patent Publication No. 56-104,877 discloses a process for monoepoxidizing 1,5,9-cyclododecatriene to produce 1,2-epoxy-5,9-cyclododecadiene. In this process, 1,5,9-cyclododecatriene is brought into contact with hydrogen peroxide in the presence of a performic acid produced from the reaction of formic acid with hydrogen peroxide in the epoxidation reaction system. This process is disadvantageous in that the yield of the target 1,2-epoxy-5,9-cyclododecadiene based on the amount of the peroxide is low and formic acid, which is very corrosive, must be employed.

Also, Japanese Examined Patent Publication No. 45-13,331 discloses a process for monoepoxidizing 1,5,9-cyclododecatriene with hydrogen peroxide in the presence of a catalyst comprising selenium dioxide, selenious acid or an alkyl selenite ester. This process is disadvantageous in that the necessary reaction time is too long and selenium compounds having a high toxity must be used as a catalyst. Further, Bull. Chem. Soc. Jpn., 42, 1604 (1969) discloses a process for monoepoxidizing 1,5,9-cyclododecatriene with a 90% aqueous hydrogen peroxide solution in the presence of a catalyst consisting of tungstic acid. This process is also disadvantage in that a high concentration hydrogen peroxide, which is very dangerous must be used, the necessary reaction time is long and the yield of the target product is low in comparison with the amount of the peroxide used. Namely, the known prior processes for producing 1,2-epoxy-5,9-cyclododecadiene are unsatisfactory as industrially usable processes.

SUMMARY OF THE INVENTION

An object of the present invention is to provide a process for producing 1,2-epoxy-5,9-cyclododecadiene by epoxidizing 1,5,9-cyclododecatriene with hydrogen peroxide, with a high selectivity to 1,2-epoxy-5,9-cyclododecadiene, and with high efficiency and productivity.

Another object of the present invention is to provide a process for continuously producing 1,2-epoxy-5,9-cyclododecadiene by epoxidizing 1,5,9-cyclododecatriene with hydrogen peroxide, in a plurality of oxidation reactors connected to each other in series.

The above-mentioned objects can be attained by the process of the present invention for producing 1,2-epoxy-5,9-cyclododecadiene, which comprises:

epoxidizing 1,5,9-cyclododecatriene with hydrogen peroxide by using a continuous multi-stage oxidation apparatus in such a manner that (1) in a first reactor of the oxidation apparatus, 1,5,9-cyclododecatriene, hydrogen peroxide and a catalyst are introduced thereinto, to epoxidize a portion of the introduced 1,5,9-cyclododecatriene into 1,2-epoxy-5,9-cyclododecadiene, and the resultant reaction mixture comprising the produced 1,2-epoxy-5,9-cyclododecadiene, the non-reacted 1,5,9-cyclododecatriene and hydrogen peroxide and the catalyst is delivered therefrom; (2) the reaction mixture delivered from the first reactor is passed through one or more reactors succeeding to the first reactor, to further epoxidize the non-reacted 1,5,9-cyclododecatriene and to increase the amount of 1,2-epoxy-5,9-cyclododecadiene; and (3) a final reaction mixture produced in a rearend reactor and comprising the produced 1,2-epoxy-5,9-cyclododecadiene in an increased amount, the non-reacted 1,5,9-cyclododecatriene and hydrogen peroxide and the catalyst is delivered from the oxidation apparatus.

The process of the present invention optionally further comprises:

subjecting the final reaction mixture delivered from the oxidation apparatus to an isolation and refining procedure to collect 1,2-epoxy-5,9-cyclododecadiene and to recover the non-reacted 1,5,9-cyclododecatriene; and recycling the recovered 1,5,9-cyclododecatriene to the first reactor to reuse it for the production of 1,2-epoxy-5,9-cyclododecadiene.

In the 1,2-epoxy-5,9-cyclododecadiene-producing process of the present invention, the catalyst for the epoxidation preferably comprises at least one member selected from the group consisting of mixtures and complex compounds of at least one tungsten compound with at least one ionic compound selected from the group consisting of (1) quaternary ammonium salt compounds of the general formula (I):

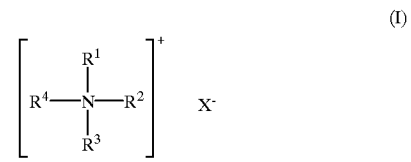

wherein $R^1$, $R^2$, $R^3$ and $R^4$ respectively and independently from each other represent a member selected from the group consisting of alkyl groups having 1 to 18 carbon atoms, aralkyl groups having 7 to 12 carbon atoms and aryl group having 6 to 8 carbon atoms, which alkyl, aralkyl and aryl groups may have at least one substituent, and X represents a member selected from the group consisting of atoms and atomic groups capable of forming a counter anion to a quaternary ammonium ion, and (2) quaternary pyridinium salt compounds of the general formula (II):

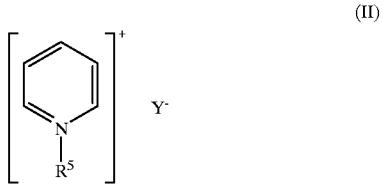

wherein $R^5$ represents a member selected from the group consisting of alkyl groups having 1 to 18 carbon atoms, aralkyl groups having 7 to 12 carbon atoms and aryl groups having 6 to 8 carbon atoms, which alkyl, aralkyl and aryl groups may be substituted, and Y represent a member selected from the group consisting of atoms and atomic groups capable of forming a counter anion to a quaternary pyridinium ion.

In the process of the present invention, optionally, a mineral acid is fed into the first reactor of the oxidation apparatus whereby, in each of the reactors, the monoepoxidation reaction of 1,5,9-cyclododecatriene with hydrogen peroxide in the presence of the catalyst is accelerated.

In an embodiment of the process of the present invention for producing 1,2-epoxy-5,9-cyclododecadiene, 1,5,9-cyclododecatriene is epoxidized by bringing 1,5,9-cyclododecatriene into contact with hydrogen peroxide in the presence of (A) at least one tungsten compound and (B) at least one member selected from the group consisting of (1) quaternary ammonium salt compounds of the general formula (I):

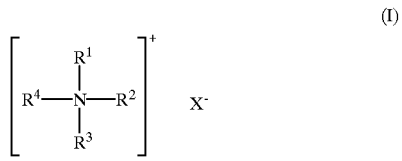

wherein $R^1$, $R^2$, $R^3$ and $R^4$ respectively and independently from each other represent a member selected from the group consisting of alkyl groups having 1 to 18 carbon atoms, aralkyl groups having 7 to 12 carbon atoms and aryl group having 6 to 8 carbon atoms which alkyl, aralkyl and aryl groups may be substituted, and X represents a member selected from the group consisting of atoms and atomic groups capable of forming a counter anion to a quaternary ammonium ion, and (2) quaternary pyridinium salt compounds of the general formula (II):

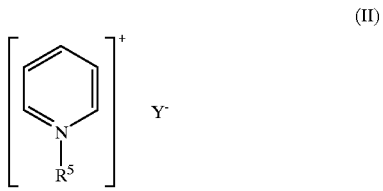

wherein $R^5$ represents a member selected from the group consisting of alkyl groups having 1 to 18 carbon atoms, aralkyl groups having 7 to 12 carbon atoms and aryl groups having 6 to 8 carbon atoms, which alkyl, aralkyl and aryl groups may be substituted, and Y represent a member selected from the group consisting of atoms and atomic groups capable of forming a counter anion to a quaternary pyridinium ion.

BRIEF DESCRIPTION OF THE DRAWING

FIG. 1 is a flow sheet showing an embodiment of the process of the present invention using a continuous multi-stage oxidation apparatus.

DESCRIPTION OF THE PREFERRED EMBODIMENTS

In the process of the present invention, the reaction apparatus for epoxidizing 1,5,9-cyclododecatriene is a continuous multi-stage oxidation apparatus having a plurality of, preferably 3 to 8 oxidation reactors connected to each other in series. The oxidation reactors may be present independent from each other and connected to each other in series through connecting conduits or may be formed by portioning a reaction vessel into two or more chambers connected to each other in series through connecting paths. The forms and sizes of the reactors may be the same as or different from each other.

The process for producing 1,2-epoxy-5,9-cyclododecadiene of the present invention will be explained in detail by referring to the attached FIG. 1.

In FIG. 1 showing a flow sheet of an embodiment of the process of the present invention, a continuous multi-stage oxidation apparatus 1a is used. The oxidation apparatus 1a shown in FIG. 1 has three reactors, namely a first reactor 1, a second reactor 10 and a rearend reactor 20 which are connected to each other in series. The first reactor 1 is connected to a supply line 2 for 1,5,9-cyclododecatriene, a supply line 3 for a tungsten compound for providing a catalyst, a supply line 4 for a quaternary ammonium salt or a quaternary pyridinium salt for proving together with the tungsten compound a catalyst, a supply line 5 for a mineral acid and a supply line 6 for hydrogen peroxide.

In the first reactor 1, a portion of 1,5,9-cyclododecatriene fed into the first reactor 1 is monoepoxidized with hydrogen peroxide in the presence of a catalyst provided from the tungsten compound and the quaternary ammonium salt or quaternary pyridinium salt, and optionally in the presence of a reaction accelerator consisting the mineral acid, to produce a first reaction mixture comprising the produced 1,2-epoxy-5,9-cyclododecadiene, the non-reacted 1,5,9-cyclododecatriene and hydrogen peroxide, the catalyst and optionally the mineral acid. The resultant first reaction mixture is delivered from the first reactor 1 and passed through one or more reactors succeeding to the first reactor 1, for example, a second reactor 10 connected to an outlet of the first reactor 1 through a connecting conduit 7 and a rearend reactor 20 connected to an outlet of the second reactor 10 through a connecting conduit 11, as shown in FIG. 1. In each of the succeeding reactors 10 and 20, portions of the non-reacted 1,5,9-cyclododecatriene and hydrogen peroxide are reacted with each other in the presence of the catalyst and optionally the mineral acid to produce 1,2-epoxy-5,9-cyclododecadiene, and thus to increase the amount of 1,2-epoxy-5,9-cyclododecadiene in the reaction mixture.

In the rearend reactor 20, the resultant reaction mixture comprising the produced 1,2-epoxy-5,9-cyclododecadiene in an increased amount, the non-reacted 1,5,9-cyclododecatriene and hydrogen peroxide, the catalyst and optionally the mineral acid is delivered from the oxidation apparatus 1a through a delivery line 21.

In the process of the present invention, the target 1,2-epoxy-5,9-cyclododecadiene is produced with a high selectivity thereto and with high yield and productivity.

In the process of the present invention, the monoepoxidation reaction of 1,5,9-cyclododecatriene with hydrogen peroxide in the presence of the catalyst in each reactor is preferably carried out at a reaction temperature of 20 to 120° C., more preferably 30 to 120° C.

The monoepoxidation reaction in each reactor is usually carried out under the ambient atmospheric pressure. However, the monoepoxidation reaction in each reactor may be carried out under an increased pressure or under a reduced pressure.

In the process of the present invention, the epoxidation reaction of 1,5,9-cyclododecatriene with hydrogen peroxide in the oxidation apparatus is preferably carried out to such an extend that the conversion of 1,5,9-cyclododecatriene is 4 to 50%, more preferably 10 to 30%. Particularly, in the first reactor, the above-mentioned conversion is preferably 1 to 30%, more preferably 3 to 20%. On the other hand, the conversion of hydrogen peroxide is preferably controlled to 90 to 100%, more preferably 95 to 100%, at the outlet of the rearend reactor of the oxidation apparatus, and to 10 to 80%, more preferably 10 to 70%, at the outlet of the first reactor of the oxidation apparatus.

Also, in the process of the present invention, the total molar amount of hydrogen peroxide fed during the entire monooxidation procedure in the oxidation apparatus is preferably controlled to 0.04 to 0.55 times, more preferably 0.10 to 0.55 times, still more preferably 0.10 to 0.30 times the molar amount of 1,5,9-cyclododecatriene fed into the first reactor, to produce the target 1,2-epoxy-5,9-cyclododecadiene at a high selectivity thereto.

The catalyst usable for the epoxidation reaction in accordance with the process of the present invention preferably comprises at least one member selected from the group consisting of mixtures and complex compounds of at least one tungsten compound with at least one ionic compound selected from the group consisting of (1) quaternary ammonium salts of the general formula (I) and (2) quaternary pyridinium salts of the general formula (II).

The tungsten-containing complex compounds are preferably prepared from at least one tungsten compound, at least one quaternary ammonium salt of the formula (I) or at least one quaternary pyridium salt of the formula (II), and hydrogen peroxide, and optionally a mineral acid. Especially, the complex compounds for the catalyst preferably contain phosphorus atoms.

The tungsten compounds usable for the catalyst for the epoxidation reaction of the process of the present invention are preferably selected from tungsten atom-containing inorganic acids and salts thereof, for example, tungstic acid and its salts, for example, sodium tungstate, potassium tungstate, lithium tungstate and ammonium tungstate; dodecatungstates, for example, sodium dodecatungstate, potassium dodecatungstate and ammonium dodecatungstate; tungsten atom-containing heteropolyacids and salts thereof, for example, phosphotungstic acid, sodium phosphotungstate, silicotungstic acid, sodium silicotungstate, phosphovanadotungstic acid and phosphomolybdotungstic acid. Preferably, the tungstic acid, sodium tungstate, potassium tungstate and phosphotungstate are used for the process of the present invention. The above-mentioned tungsten compounds may be used alone or in a mixture of two or more thereof.

In the catalyst for the process of the present invention, the tungsten compounds are preferably employed in an amount of 0.0007 to 5% by weight, more preferably 0.002 to 3% by weight, in terms of tungsten atoms, based on the amount of 1,5,9-cyclododecatriene fed into the epoxidation reaction procedure in the oxidation apparatus.

In the process of the present invention, the catalyst preferably comprises, in addition to the tungsten compounds, the quaternary ammonium salt (1) of the general formula (I) and/or the quaternary pyridinium salt (2) of the general formula (II), for the production of 1,2-epoxy-5,9-cyclododecadiene by the monoepoxidation of 1,5,9-cyclododecatriene.

In the formula (I) for the quaternary ammonium salts (1):

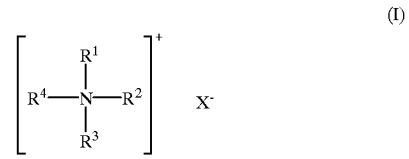

$R^1$, $R^2$, $R^3$ and $R^4$ respectively and independently from each other represent a member selected from the group consisting of alkyl groups having 1 to 18 carbon atoms, aralkyl groups having 7 to 12 carbon atoms and aryl group having 6 to 8 carbon atoms, which alkyl, aralkyl and aryl groups may have at least one substituent selected from, for example, alkyl groups having 1 to 4 carbon atoms, halogen atoms, a hydroxyl group, amino groups and a carboxyl group, and X represents a member selected from the group consisting of atoms and atomic groups capable of forming a counter anion to a quaternary ammonium ion.

In the general formula (II) for the quaternary pyridinium salts:

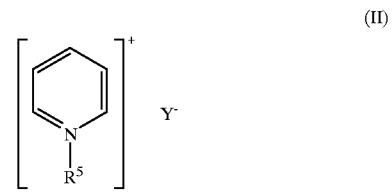

$R^5$ represents a member selected from the group consisting of alkyl groups having 1 to 18 carbon atoms, aralkyl groups having 7 to 12 carbon atoms and aryl groups having 6 to 8 carbon atoms, which alkyl, aralkyl and aryl groups may be substituted, and Y represent a member selected from the group consisting of atoms and atomic groups capable of forming a counter anion to a quaternary pyridinium ion.

The atoms and atomic groups capable of forming a counter anion to a quaternary ammonium ion or quaternary pyridinium ion and represented by X or Y are preferably selected from halogen atoms, a $HSO_4$ group, a $H_2PO_4$ group, a $NO_3$ group, a $BF_4$ group, a $OCOH$ group and a $OCOCH_3$ group, more preferably hydrogen atoms, still more preferably a chlorine atom.

The quaternary ammonium salts (1) of the general formula (I) usable for the catalyst for the process of the present invention include, for example, quaternary ammonium halides, for example, trioctylmethyl ammonium chloride, tridecylmethyl ammonium chloride, trioctylmethyl ammonium bromide, benzyldimethyltetradecyl ammonium chloride, benzyltriethyl ammonium chloride, dimethyldidodecyl ammonium chloride, benzyltributyl ammonium chloride, benzyltributyl ammonium iodide, and phenyltrimethyl ammonium chloride; quaternary ammonium hydrogen sulfates, for example, trioctylmethyl ammonium hydrogen sulfate; quaternary ammonium perchlorates, for example, trioctylmethyl ammonium perchlorate; quaternary ammonium dihydrogen phosphates, for example, trioctylmethyl ammonium dihydrogen phosphate; quaternary ammonium nitrates, for example, trioctylmethyl ammonium nitrate; quaternary ammonium hydrosilicofluorates, for example, trioctylmethyl ammonium hydrosilicofluorate; and quaternary ammonium acetates, for example, trioctylmethyl ammonium acetate. Among the above-mentioned salts, the quaternary ammonium halides are preferably employed and particularly, the trioctylmethyl ammonium chloride and tridecylmethyl ammonium chloride are more preferably used for the process of the present invention.

The quaternary pyridinium salts usable for the catalyst for the process of the present invention include, for example, quaternary pyridinium halides, for example, cetylpyridinium chloride and cetylpyridinium bromide; and quaternary pyridinium hydrogen sulfates, for example, laurylpyridinium hydrogen sulfate. Preferably, the quaternary pyridinium halides are used and more preferably, the cetylpyridinium chloride is employed for the catalyst.

The ionic compound comprising at least one member selected from the quaternary ammonium salts (1) of the formula (I) and the quaternary pyridinium salts (2) of the formula (II) is preferably employed in an amount of 0.001 to 4% by weight, more preferably 0.003 to 2.5% by weight, based on the amount of 1,5,9-cyclododecatriene fed to the oxidation apparatus.

The quaternary ammonium salts (1) and the quaternary pyridinium salts (2) may be employed alone or in a mixture of two or more thereof.

In the process of the present invention, there is no limitation to the concentration of hydrogen peroxide fed into the first reactors of the oxidation apparatus. However, in consideration of the safety in handling and the economical efficiency, the hydrogen peroxide is preferably used in the state of an aqueous solution in a concentration thereof of 3 to 70% by weight. Also, the hydrogen peroxide is preferably employed in a molar amount of 0.04 to 0.55 times, more preferably 0.10 to 0.55 times, still more preferably 0.10 to 0.30 times the molar amount of 1,5,9-cyclododecatriene.

In the process of the present invention, optionally, a mineral acid is fed into a first reactor of the oxidation apparatus, to enhance the reaction rate, and the selectivity of 1,2-epoxy-5,9-cyclododecadiene.

The mineral acid usable for the process of the present invention comprises at least one member selected from, for example, phosphoric acid, sulfuric acid, hydrochloric acid, perchloric acid, hexaflurosilicic acid, nitric acid and tetrafluorosilicic acid. Preferably, phosphoric acid and/or sulfuric acid is used for the mineral acid. The above-mentioned inorganic acids may be used alone or in a mixture of two or more thereof. The mineral acid is preferably used in an amount of 15% by weight or less, more preferably 10% by weight or less, based on the weight of 1,5,9-cyclododecatriene fed into the first reactor of the oxidation apparatus.

In the epoxidation reaction of the process of the present invention, an organic solvent may be used as a reaction medium. There is no limitation to the type of the organic solvent as long as the organic solvent is not evenly mixed with water and does not hinder the epoxidation reaction of 1,5,9-cyclododecatriene with hydrogen peroxide. For example, the organic solvent usable as a reaction medium for the process of the present invention comprises at least one member selected from halogenated aliphatic hydrocarbons, for example, chloroform, dichloroethane and dichloromethane; non-halogenated aliphatic hydrocarbons, for example, cyclohexane and n-heptane; non-halogenated aromatic hydrocarbons, for example, benzene, toluene and xylene; and halogenated aromatic hydrocarbons, for example, chlorobenzene. These organic solvents may be employed alone or in a mixture of two or more thereof and the organic solvents are preferably used in an amount of 30% by weight or less, more preferably 20% by weight or less, based on the amount of 1,5,9-cyclododecatriene fed to the process of the present invention.

After the epoxidation procedure in the oxidation apparatus is completed, as shown in FIG. 1, the resultant reaction mixture obtained in the rearend reactor and comprising the obtained 1,2-epoxy-5,9-cyclododecadiene, the non-reacted 1,5,9-cyclododecatriene and hydrogen peroxide, the catalyst and optionally the mineral acid is withdrawn from the rearend reactor 20 through a delivery line 21, and collected.

In the process of the present invention, optionally, the final reaction mixture delivered from the rearend reactor is subjected to an isolation refining procedure (not shown in FIG. 1), to collect the produced 1,2-epoxy-5,9-cyclododecadiene and to recover the non-reacted 1,5,9-cyclododecatriene. In the isolation-refining procedure, the final reaction mixture delivered from the rearend reactor is fed into an oil/water separating vessel (not shown in FIG. 1) in which an oily 1,5,9-cyclododecatriene phase (oil phase) fraction containing 1,2-epoxy-5,9-cyclododecadiene is separated from an aqueous phase fraction, then the separated oil phase fraction is fed into a recovery column (not shown in FIG. 1) for recovering 1,5,9-cyclododecatriene. In the recovery column, the 1,5,9-cyclododecatriene, 1,2-epoxy-5, 9-cyclododecadiene and other components are separated from each other by conventional distillation procedure. For example, in the recovery column, first, if necessary, a light fraction such as the organic solvent is removed from the oil phase fraction, and then the non-reacted 1,5,9-cyclododecatriene is recovered as a distilled fraction. Then, the residual fraction containing, as a principal component, the target 1,2-epoxy-5,9-cyclododecadiene is fed to a fractionation distillation column (not shown in FIG. 1) in which the target 1,2-epoxy-5,9-cyclododecadiene is refined and collected as a distilled fraction having a high degree of purification.

The isolation-refining procedure of the process of the present invention, the non-reacted 1,5,9-cyclododecatriene recovered by the above-mentioned distillation in the recovery column is preferably recycled into the first reactor of the oxidation apparatus and reused in the process of the present invention for producing 1,2-epoxy-5,9-cyclododecadiene. The recovered 1,5,9-cyclododecatriene is returned preferably in a weight of 1 to 24 times, more preferably 2 to 9 times the weight of fresh 1,5,9-cyclododecatriene fed into the first reactor. In this case, the returned 1,5,9-cyclododecatriene preferably contains 1,2-epoxy-5,9-cyclododecadiene in a limited amount of 5.5% by weight or less.

In an embodiment of the process of the present invention for producing 1,2-epoxy-5,9-cyclododecadiene, 1,5,9-cyclododecatriene is epoxidized by bringing 1,5,9-cyclododecatriene into contact with hydrogen peroxide in the presence of (A) at least one tungsten compound and (B) at least one member selected from the group consisting of (1) quaternary ammonium salt compounds of the general formula (I):

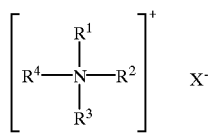

wherein $R^1$, $R^2$, $R^3$ and $R^4$ respectively and independently from each other represent a member selected from the group consisting of alkyl groups having 1 to 18 carbon atoms, aralkyl groups having 7 to 12 carbon atoms and aryl group having 6 to 8 carbon atoms which alkyl, aralkyl and aryl groups may be substituted, and X represents a member selected from the group consisting of atoms and atomic groups capable of forming a counter anion to a quaternary ammonium ion, and (2) quaternary pyridium salt compounds of the general formula (II):

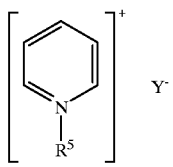

wherein $R^5$ represents a member selected from the group consisting of alkyl groups having 1 to 18 carbon atoms, aralkyl groups having 7 to 12 carbon atoms and aryl groups having 6 to 8 carbon atoms, which alkyl, aralkyl and aryl groups may be substituted, and Y represent a member selected from the group consisting of atoms and atomic groups capable of forming a counter anion to a quaternary pyridinium ion.

In this embodiment, 1,2-epoxy-5,9-cyclododecadiene can be catalytically produced from 1,5,9-cyclododecatriene at a high reaction rate and with a high yield which have not been obtained in the prior art.

EXAMPLES

The process of the present invention will be further illustrated by the following examples.

Example 1

Production of 1,2-epoxy-5,9-cyclododecadiene from 1,5,9-cyclododecatriene was carried out by using a continuous multi-stage oxidation apparatus comprising three reactors connected to each other in series, as shown in FIG. 1, and each having an agitater. An oil/water separating vessel (not shown in FIG. 1), a recovery column for non-reacted 1,5,9-cyclododecatriene (not shown in FIG. 1) and a refining column for the produced 1,2-epoxy-5,9-cyclododecadiene (not shown in FIG. 1) were connected to the rearend reactor.

Each of the three reactors of the oxidation apparatus had an inner volume of 3.1 liters.

Into the first reactor of the oxidation apparatus were fed 1,5,9-cyclododecatriene (a starting material) at a feed rate of 7937 g/hr, phosphotungstic acid (a catalyst component) at a feed rate of 1.39 g/hr (corresponding to 1.07 g/hr in terms of tungsten atom), trioctylmethyl ammonium chloride (a catalyst component) at a feed rate of 1.60 g/hr, and a 60% by weight aqueous hydrogen peroxide solution (an oxidizing agent) at a feed rate of 695 g/hr (corresponding to 417 g/hr in terms of hydrogen peroxide). The fed compounds were mixed with each other in the first reactor and subjected to a first epoxidation reaction at a reaction temperature of 75° C. for a resident time of 20 minutes. The resultant reaction mixture was delivered from the first reactor and then fed into the second reactor through a connecting conduit.

A sample of the reaction mixture delivered from the first reactor was taken and subjected to an oil/water separating procedure by which an oil phase fraction comprising the non-reacted 1,5,9-cyclododecatriene and the produced 1,2-epoxy-5,9-cyclododecadiene was separated from an aqueous phase fraction comprising the non-reacted hydrogen peroxide. The oil phase fraction was subjected to a gas chromatographic analysis and the aqueous phase fraction was subjected to an iodometeric analysis, to determine the composition of the reaction mixture delivered from the first reactor, in terms of flow rate of each compound.

The reaction mixture delivered from the first reactor comprised the non-reacted 1,5,9-cyclododecatriene in a flow rate of 6719 g/hr (corresponding to a conversion thereof of 15.3%), the produced 1,2-epoxy-5,9-cyclododecadiene in a flow rate of 1260 g/hr, the nonreacted hydrogen peroxide in a flow rate of 130 g/hr (corresponding to a conversion thereof of 68.8%), and the above-mentioned catalyst components.

The reaction mixture delivered from the first reactor was fed into a second reactor through an inlet located in an upper portion of the second reactor, and was subjected to a second epoxidation reaction at a reaction temperature of 75° C. for a residing time of 20 minutes. The resultant reaction mixture was delivered from the second reactor and fed into a rearend reactor.

A sample of the reaction mixture delivered from the second reactor was collected at an outlet of the second reactor and subjected to the same analysises as those of the first reactor. The reaction mixture delivered from the second reactor comprised the non-reacted 1,5,9-cyclododecatriene in a flow rate of 6299 g/hr, the produced 1,2-epoxy-5,9-cyclododecadiene in a flow rate of 1682 g/hr and the non-reacted hydrogen peroxide in a flow rate of 31 g/hr.

The reaction mixture delivered from the second reactor was fed into an upper portion of the rearend reactor and was subjected to a final epoxidation reaction at a reaction temperature of 75° C. for a residing time of 20 minutes.

The resultant reaction mixture in the rearend reactor was delivered from the rearend reactor through an outlet of the rearend reactor and a delivery line connected to the outlet. A sample of the delivered final reaction mixture was subjected to the same analyses as those of the first reactor. The final reaction mixture delivered from the rearend reactor comprised the non-reacted 1,5,9-cyclododecatriene at a flow rate of 6206 g/hr, the target 1,2-epoxy-5,9-cyclododecadiene at a flow rate of 1774 g/hr and the non-reacted hydrogen peroxide at a flow rate of 5 g/hr.

In the continuous multi-stage oxidation apparatus, the epoxidation reaction was continuously carried out for a total time of 50 hours, and a final reaction liquid was obtained in an amount of 431 kg.

The final reaction mixture delivered from the rearend reactor of the oxidation apparatus was fed into an oil/water separating vessel. In the separating vessel, 406 kg of an oil phase fraction and 25 kg of an aqueous phase fraction are separated from each other. A sample of the oil phase fraction was subjected to a gas chromatographic analysis. As a result, the oil phase fraction contained 76.4% by weight of 1,5,9-cyclododecatriene and 21.9% by weight of the target 1,2-epoxy-5,9-cyclododecadiene.

Namely, it was confirmed that, in the continuous multi-stage epoxidation procedure, the amount of the non-reacted 1,5,9-cyclododecatriene was 310.2 kg, and the amount of 1,5,9-cyclododecatriene consumed by the reaction was 86.8 kg, and the amount of the produced 1,2-epoxy-5,9-cyclododecadiene was 88.9 kg.

On the other hand, a sample of the aqueous phase fraction was subjected to an iodometric analysis. As a result, it was confirmed that the non-reacted hydrogen peroxide remaining in the final reaction mixture was 0.25 kg, and the amount of hydrogen peroxide consumed by the epoxidation reaction was 20.55 kg.

In the result of the continuous multi-stage epoxidation procedure, the conversion of 1,5,9-cyclododecatriene was 21.9 molar %, the selectivity to 1,2-epoxy-5,9-cyclododecadiene based on the molar amount of the consumed 1,5,9-cyclododecatriene was 93.2 molar %, the conversion of the hydrogen peroxide was 98.8 molar %, and the selectivity to 1,2-epoxy-5,9-cyclododecadiene based on the molar amount of the consumed hydrogen peroxide was 84.0 molar %. In this continuous multi-stage epoxidation procedure, the production rate of 1,2-epoxy-5,9-cyclododecadiene per unit volume (liter) of the reactors was 190.8 g/liter.hr.

The separated oil phase fraction was fed into a recovery column for the non-reacted 1,5,9-cyclododecatriene and was subjected to reduced pressure distillation under a pressure of 3.0 kPa at a temperature of 118° C. As a result, 310 kg of 1,5,9-cyclododecatriene having a degree of purity of 98.4% and containing 1.4% by weight of 1,2-epoxy-5,9-cyclododecadiene was selected from a residual oil phase fraction and recovered.

The residual oil phase fraction was fed into a refining column for 1,2-epoxy-5,9-cyclododecadiene and was subjected to a reduced pressure refining distillation under a pressure of 1.3 kPa at a temperature of 130° C. As a result, a refined 1,2-epoxy-5,9-cyclododecadiene having a degree of purity of 99.6% was collected in an amount of 81 kg.

Example 2

The same procedures and analyses as in Example 1 were carried out with the following exceptions.

The oil phase fraction recovered by the 1,5,9-cyclododecatriene-recovery column and containing the non-reacted 1,5,9-cyclododecatriene having a degree of purity of 98.4% (and containing 1.4% by weight of 1,2-epoxy-5,9-cyclododecadiene) was fed at a feed rate of 6276 g/hr, together with fresh 1,5,9-cyclododecatriene at a feed rate of 1750 g/hr, into the first reactor. The total feed rate of 1,5,9-cyclododecatriene was 8026 g/hr.

In the analysis results of the reaction mixture delivered from the rearend reactor, the conversion of 1,5,9-cyclododecatriene was 21.8 molar %, the selectivity to 1,2-epoxy-5,9-cyclododecadiene based on the molar amount of the consumed 1,5,9-cyclododecatriene was 93.1 molar %, the conversion of the hydrogen peroxide was 98.8 molar %, and the selectivity to 1,2-epoxy-5,9-cyclododecadiene based on the molar amount of the consumed hydrogen peroxide was 83.6 molar %. In this continuous multi-stage epoxidation procedure, the production rate of 1,2-epoxy-5,9-cyclododecadiene per unit volume (liter) of the reactors was 190.3 g/liter.hr.

Example 3

The same procedures for the production of 1,2-epoxy-5,9-cyclododecadiene and the same analyses as those in Example 1 were carried out by using the same oxidation apparatus and isolate-refining apparatus as in Example I with the following exceptions.

The inner volume of the rearend reactor was changed from 3.1 liters to 6.2 liters.

Into an upper portion of the first reactor of the oxidation apparatus were fed 1,5,9-cyclododecatriene (a starting material) at a feed rate of 7979 g/hr, sodium tangstate dihydrate (a catalyst component) at a feed rate of 1.61 g/hr (corresponding to 0.90 g/hr in terms of tungsten atom), trioctylmethyl ammonium chloride (a catalyst component) at a feed rate of 1.60 g/hr, phosphoric acid at a feed rate of 1.61 g/hr and a 60% by weight aqueous hydrogen peroxide solution (an oxidizing agent) at a feed rate of 701 g/hr (corresponding to 421 g/hr in terms of hydrogen peroxide). The fed compounds were mixed with each other in the first reactor and subjected to a first epoxidation reaction at a reaction temperature of 65° C. for a resident time of 20 minutes. The resultant reaction mixture was delivered from the first reactor and then fed into the second reactor through a connecting conduit.

A sample of the reaction mixture delivered from the first reactor was collected and subjected to the same analysis procedures as in Example 1.

The reaction mixture delivered from the first reactor comprised the non-reacted 1,5,9-cyclododecatriene at a flow rate of 7187 g/hr (corresponding to a conversion thereof of 9.9%), the produced 1,2-epoxy-5,9-cyclododecadiene at a flow rate of 841 g/hr, the non-reacted hydrogen peroxide at a flow rate of 228 g/hr (corresponding to a conversion thereof of 45.8%), and the above-mentioned catalyst components.

The reaction mixture delivered from the first reactor was fed into a second reactor through an inlet located in an upper portion of the second reactor, and was subjected to a second epoxidation reaction at a reaction temperature of 65° C. for a resident time of 20 minutes. The resultant reaction mixture was delivered from the second reactor and fed into a rearend reactor.

A sample of the reaction mixture delivered from the second reactor was collected at an outlet of the second reactor and subjected to the same analyses as those of the first reactor. The reaction mixture delivered from the second reactor comprised the non-reacted 1,5,9-cyclododecatriene at a flow rate of 6800 g/hr, the produced 1,2-epoxy-5,9-cyclododecadiene at a flow rate of 1241 g/hr and the non-reacted hydrogen peroxide at a flow rate of 141 g/hr.

The reaction mixture delivered from the second reactor was fed into an upper portion of the rearend reactor and was subjected to a final epoxidation reaction at a reaction temperature of 75° C. for a resident time of 40 minutes.

The resultant reaction mixture in the rearend reactor was delivered from the rearend reactor through an outlet of the rearend reactor and a delivery line connected to the outlet. A sample of the delivered final reaction mixture was subjected to the same analyses as those of the first reactor. The final reaction mixture delivered from the rearend reactor comprised the non-reacted 1,5,9-cyclododecatriene at a flow rate of 6217 g/hr, the target 1,2-epoxy-5,9-cyclododecadiene at a flow rate of 1835 g/hr and the non-reacted hydrogen peroxide at a flow rate of 6 g/hr.

In the result of the continuous multi-stage epoxidation procedure, the conversion of 1,5,9-cyclododecatriene was 22.1 molar %, the selectivity to 1,2-epoxy-5,9-cyclododecadiene based on the molar amount of the consumed 1,5,9-cyclododecatriene was 94.6 molar %, the conversion of the hydrogen peroxide was 98.0 molar %, and the selectivity to 1,2-epoxy-5,9-cyclododecadiene based on the molar amount of the consumed hydrogen peroxide was 86.7 molar %. In this continuous multi-stage epoxidation procedure, the production rate of 1,2-epoxy-5,9-cyclododecadiene per unit volume (liter) of the reactors was 197.1 g/liter.hr.

Example 4

Production of 1,2-epoxy-5,9-cyclododecadiene from 1,5,9-cyclododecatriene was carried out by using a single epoxidation reactor having an inner volume of 31.0 liters, and the same separation and refining apparatus is in Example 1.

Into the single epoxidation reactor were fed 1,5,9-cyclododecatriene (a starting material) at a feed rate of 3969 g/hr, phosphotungstic acid (a catalyst component) at a feed rate of 0.70 g/hr (corresponding to 0.54 g/hr in terms of tungsten atom), trioctylmethyl ammonium chloride (a catalyst component) at a feed rate of 0.80 g/hr, and a 60% by weight aqueous hydrogen peroxide solution (an oxidizing agent) in a feed rate of 348 g/hr (corresponding to 209 g/hr in terms of hydrogen peroxide). The fed compounds were mixed with each other in the first reactor and subjected to an epoxidation reaction at a reaction temperature of 75° C. for a resident time of 388 minutes. The resultant reaction mixture was delivered from the epoxidation reactor.

A sample of the reaction mixture delivered the reactor was taken and subjected to the same analyses as in Example 1.

The reaction mixture delivered from the epoxidation reactor comprised the non-reacted 1,5,9-cyclododecatriene at a flow rate of 3116 g/hr, the produced 1,2-epoxy-5,9-cyclododecadiene at a flow rate of 855 g/hr, the non-reacted hydrogen peroxide at a flow rate of 7 g/hr, and the above-mentioned catalyst components.

From the analysis results of the delivered reaction mixture, it was confirmed that the conversion of 1,5,9-cyclododecatriene was 21.5 molar %, the selectivity to 1,2-epoxy-5,9-cyclododecadiene based on the molar amount of the consumed 1,5,9-cyclododecatriene was 91.2 molar %, the conversion of the hydrogen peroxide was 97.0 molar %, and the selectivity to 1,2-epoxy-5,9-cyclododecadiene based on the molar amount of the consumed hydrogen peroxide was 80.6 molar %. In this epoxidation procedure, the production rate of 1,2-epoxy-5,9-cyclododecadiene per unit volume (liter) of the reactors was 27.6 g/liter.hr.

This production rate of 1,2-epoxy-5,9-cyclododecadiene per unit volume of the reactor in Example 4 was significantly lower than that in Examples 1 to 3.

In the process of the present invention for producing 1,2-epoxy-5,9-cyclododecadiene by epoxidizing 1,5,9-cyclododecatriene with hydrogen peroxide, the target 1,2-epoxy-5,9-cyclododecadiene can be prepared with high selectivity by a continuous multi-stage procedure. The process of the present invention can be utilized for industrial practice with a high productivity.

Example 5

A glass two neck flask having a capacity of 100 ml and equipped with a reflux condenser and a thermometer and was charged with a mixture of 26.25 g (0.162 moles) of 1,5,9-cyclododecatriene, with 0.004 g of phosphotungstic acid, 0.04 g of Aliquat 336 (trademark, made by ALDRICH CO., and comprising a mixture of trioctylmethylammonium chloride with tridecylmethylammonium chloride), 70 g (0.030 moles) of a 60 weight% aqueous hydrogen peroxide solution, and 8 g of toluene. The charged mixture in the flask was heated to a temperature of 70° C. for one hour in a nitrogen gas atmosphere, while stirring the mixture. After the reaction was completed, the reaction mixture was cooled to room temperature.

The contents of 1,5,9-cyclododecatriene and 1,2-epoxy-5,9-cyclododecadiene in the reaction mixture was determined by a gas chromatographic analysis and the content of hydrogen peroxide in the reaction mixture was determined by an iodometric analysis. From the analysis results, it was confirmed that the conversion of 1,5,9-cyclododecatriene was 18.2%, the selectivity to 1,2-epoxy-5,9-cyclododecadiene based on the consumed molar amount of the 1,5,9-cyclododecatriene was 95.0 molar %, the conversion of hydrogen peroxide was 99.9% and the selectivity to 1,2-epoxy-5,9-cyclododecadiene based on the consumed molar amount of hydrogen peroxide was 89.0 molar %.

We claim:

1. A process for producing 1,2-epoxy-5,9-cyclododecadiene, comprising epoxidizing 1,5,9-cyclododecatriene with hydrogen peroxide by using a continuous multi-stage oxidation apparatus wherein (1) in a first reactor of the oxidation apparatus, 1,5,9-cyclododecatrine, hydrogen peroxide and a catalyst are introduced thereinto, to epoxidize a portion of the introduced 1,5,9-cyclododecatriene into 1,2,-epoxy-5,9-cyclododecadiene, and the resultant reaction mixture comprising the thus-produced 1,2-epoxy-5,9-cyclododecatriene, hydrogen peroxide and the catalyst are delivered therefrom; (2) the reaction mixture delivered from the first reactor is passed through one or more reactors succeeding to the first reactor, to further epoxidize the non-reacted 1,5,9-cyclododecatriene and to increase the amount of 1,2-epoxy-5,9-cyclododecadiene; and (3) a final reaction mixture produced in a rear-end reactor and comprising the produced 1,2-epoxy-5,9-cyclododecadiene in an increased amount, the non-reacted 1,5,9-cyclododecatriene and hydrogen peroxide and the catalyst are delivered from the oxidation apparatus; subjecting the resultant reaction mixture delivered from the rear-end reactor to an isolation and refining procedure to collect 1,2-epoxy-5,9-cyclododecadiene, and to recover the non-reacted 1,5,9-cyclododecatriene; and recycling the recovered non-reacted 1,5,9-cyclododecatriene to the first reactor, to re-use it for the production of 1,2-epoxy-5,9-cyclododecadiene, the amount of the recovered non-reacted 1,5,9-cyclododecatriene recycled into the first reactor being controlled to 1 to 24 times the weight of the fresh 1,5,9-cyclododecatriene fed into the first reactor.

2. The 1,2-epoxy-5,9-cyclododecadiene-producing process as claimed in claim 1, wherein the hydrogen peroxide is fed in a molar amount of 0.04 to 0.55 times the molar amount of 1,5,9-cyclododecadiene fed into the oxidation apparatus.

3. The 1,2-epoxy-5,9-cyclododecadiene-producing process as claimed in claim 1, wherein the epoxidation reaction of 1,5,9-cyclododecatriene in the first reactor is carried out with a conversion of hydrogen peroxide of 10 to 80%.

4. The 1,2-epoxy-5,9-cyclododecadiene-producing process as claimed in claim 1, wherein the non-reacted 1,5,9-cyclododecatriene recovered by the isolation and refining procedure contains 1,2-epoxy-5,9-cyclododecadiene in an amount of 5.5% by weight or less.

5. The 1,2-epoxy-5,9-cyclododecadiene-producing process as claimed in claim 1, wherein the catalyst for the epoxidation comprises at least one member selected from the group consisting of mixtures and complex compounds of at least one tungsten compound with at least one ionic compound selected from the group consisting of (1) quaternary ammonium salts of the general formula (I):

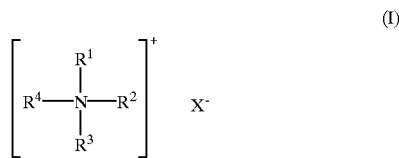

wherein $R^1$, $R^2$, $R^3$ and $R^4$ respectively and independently from each other represent a member selected from the group consisting of alkyl groups having 1 to 18 carbon atoms, aralkyl groups having 7 to 12 carbon atoms and aryl groups having 6 to 8 carbon atoms, which alkyl, aralkyl and aryl groups may have at least one substituted, and X represents a member selected from the group consisting of atoms and atomic groups capable of forming a counter anion to a quaternary ammonium ion, and (2) quaternary pyridinium salts of the general formula (II):

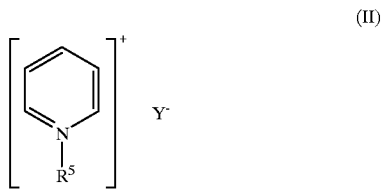

wherein $R^5$ represents a member selected from the group consisting of alkyl groups having 1 to 18 carbon atoms, aralkyl groups having 7 to 12 carbon atoms and aryl groups having 6 to 8 carbon atoms, which alkyl, aralkyl and aryl groups may be substituted, and Y represents a member selected from the group consisting of atoms and atomic groups capable of forming a counter anion to a quaternary pyridinium ion.

6. The 1,2-epoxy-5,9-cyclododecadiene-producing process as claimed in claim 5, wherein the tungsten compound is selected from the group consisting of tungsten atom-containing inorganic acids and salts thereof.

7. The 1,2-epoxy-5,9-cylododecadiene-producing process as claimed in claim 5, wherein the tungsten compound is selected from the group consisting of tungstic acid and its salts, dodecatungstates, and tungsten atom-containing heteropolyacids and salts thereof.

8. The 1,2-epoxy-5,9-cyclododecadiene-producing process as claimed in claim 5, wherein, in the catalyst, the tungsten compound is present in an amount of 0.0007 to 5% by weight, in terms of tungsten atoms, based on the amount of 1,5,9-cyclododecatriene fed into the first reactor.

9. The 1,2-epoxy-5,9-cyclododecadiene-producing process as claimed in claim 5, wherein the quaternary ammonium salts are selected from the group consisting of quaternary ammonium halides, monohydrogen sulfates, perchlorates, dihydrogen phosphates, nitrates, silicofluorides, and acetates.

10. The 1,2-epoxy-5,9-cyclododecadiene-producing process as claimed in claim 5, wherein the quaternary pyridinium salts are selected from the group consisting of quaternary pyridinium halides and monohydrogen sulfates.

11. The 1,2-epoxy-5,9-cyclododecadiene-producing process as claimed in claim 5, wherein in the catalyst, the ionic compound is present in an amount of 0.001 to 4% by weight, based on the amount of 1,5,9-cyclododecatriene fed into the first reactor.

12. The 1,2-epoxy-5,9-cyclododecadiene-producing process as claimed in claim 1, wherein the continuous multistage oxidation apparatus has 3 to 8 oxidation reactors connected to each other in series.

13. The 1,2-epoxy-5,9-cyclododecadiene-producing process as claimed in claim 1, wherein each reactor, the epoxidation reaction is carried out at a temperature of 20 to 120° C.

14. The 1,2-epoxy-5,9-cyclododecadiene-producing process as claimed in claim 1, wherein in each reactor, the epoxidation reaction of 1,5,9-cyclododecatriene is carried out with a conversion of 1,5,9-cyclododecatriene of 4 to 50%.

15. The 1,2-epoxy-5,9-cyclododecadiene-producing process as claimed in claim 1, wherein the entire epoxidation reaction in the oxidation apparatus is effected with a total conversion of hydrogen peroxide of 90 to 100%.

16. The 1,2-epoxy-5,9-cyclododecadiene-producing process as claimed in claim 1, wherein a mineral acid is further fed into the first reactor.

17. The 1,2-epoxy-5,9-cyclododecadiene-producing process as claimed in claim 16, wherein the mineral acid is fed in an amount of 15% by weight or less, based on the amount of 1,5,9-cyclododecatriene fed into the first reactor.

18. The 1,2-epoxy-5,9-cyclododecadiene-producing process as claimed in claim 16, wherein the mineral acid comprises at least one member selected from the group consisting of phosphoric acid, perchloric acid, sulfuric acid, hydrochloric acid, hexafluorosilicic acid, nitric acid, and tetrafluoroboric acid.

19. The 1,2-epoxy-5,9-cyclododecadiene-producing process as claimed in claim 1 wherein, in the isolation and refining procedure, the reaction mixture delivered from the rearend reactor is cooled and fed into an oil/water separating vessel in which an oil phase fraction containing 1,2-epoxy-5,9-cyclododecadiene and 1,5,9-cyclododecatriene is separated from an aqueous phase fraction, and the separated oil phase fraction is fed into a isolation procedure in which 1,2-epoxy-5,9-cyclododecadiene is isolated from the oil phase fraction and collected.

20. A process for producing 1,2-epoxy-5,9-cyclododecadiene, comprising epoxidizing 1,5,9-cyclododecatriene by bringing 1,5,9-cyclododecatriene into contact with hydrogen peroxide in the presence of (a) at least one tungsten compound and (B) at least one member selected from the group consisting of (1) quaternary ammonium salt compounds of the general formula (I):

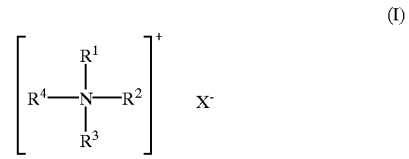

wherein $R^1$, $R^2_1$, $R^3$ and $R^4$ respectively and independently from each other represent a member selected from the group consisting of alkyl groups having 1 to 18 carbon atoms, aralkyl groups having 7 to 12 carbon atoms and aryl groups having 6 to 8 carbon atoms wherein said alkyl, aralkyl and aryl groups may have at least one substituent selected from the group consisting of alkyl groups having 1 to 4 carbon atoms, halogen atoms, a hydroxyl group, amino groups and a carboxyl group, and X represents a member selected from the group consisting of atoms and atomic groups capable of forming a counter anion to a quaternary pyridinium salt compounds of the general formula (II):

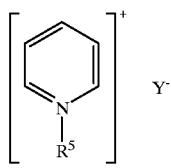

(II)

wherein $R^5$ represents a member selected from the group consisting of alkyl groups having 1 to 18 carbon atoms, aralkyl groups having 7 to 12 carbon atoms and aryl groups having 6 to 8 carbon atoms, wherein said alkyl, aralkyl and aryl groups may be substituted, and Y represents a member selected from the group consisting of atoms and atomic groups capable of forming a counter anion to a quaternary pyridinium ion.

21. The process as claimed in claim 20 for producing 1,2-epoxy-5,9-cyclododecadiene, wherein hydrogen peroxide is fed in a molar amount of 0.1 to 0.55 times the molar amount of 1,5,9-cyclododecatriene fed into the oxidation apparatus.

* * * * *

UNITED STATES PATENT AND TRADEMARK OFFICE
CERTIFICATE OF CORRECTION

PATENT NO.  :  6,043,383

DATED       :  March 28, 2000

INVENTORS   :  Nobuyuki KURODA, Mitsuo YAMANAKA, Osamu YAMAZAKI, Hirofumi TAKEMOTO, Kohei NINOMIYA, Junichi KEGIMOTO, Koji KAISO and Hideo SHIMOMURA It is certified that an error appears in the above-identified patent and that said Letters Patent is hereby as shown below:

On the title page,
Item No. [30]: Please correct Priority Date to read April <u>14</u>, 1998

Signed and Sealed this

Thirteenth Day of February, 2001

*Attest:*

NICHOLAS P. GODICI

*Attesting Officer*   Acting Director of the United States Patent and Trademark Office